United States Patent [19]

Smith et al.

[11] 4,229,420
[45] Oct. 21, 1980

[54] SURGICAL INSTRUMENT RACK

[75] Inventors: Galyn F. Smith, Schaumburg; Thomas P. Zwierszowski, Niles, both of Ill.

[73] Assignee: American Hospital Supply Corporation, Evanston, Ill.

[21] Appl. No.: 23,886

[22] Filed: Mar. 26, 1979

[51] Int. Cl.$^2$ ............................................. A61L 3/02
[52] U.S. Cl. ................................. 422/310; 128/303 R; 206/363; 206/370; 206/438; 211/1.3; 211/184; 422/104; 422/300
[58] Field of Search ............... 422/50, 58, 99, 104, 422/300, 310; 211/1.3, 183, 184; 206/363, 370, 372, 373, 438, 459, 485; 128/303 R

[56] References Cited

U.S. PATENT DOCUMENTS

| 786,758 | 4/1905 | Gutmann | 206/372 |
|---|---|---|---|
| 2,018,651 | 10/1935 | Bates | 422/300 X |
| 2,334,839 | 11/1943 | Purchas | 206/372 X |
| 2,472,028 | 5/1949 | Son | 422/300 X |
| 2,903,129 | 9/1959 | Anderson | 206/363 |
| 2,929,117 | 3/1960 | Kosswig | 422/300 X |
| 3,564,662 | 2/1971 | Dold | 422/300 |
| 3,802,844 | 4/1974 | Sendra et al. | 422/104 |
| 3,925,014 | 12/1975 | Langdon | 422/310 |
| 3,983,996 | 10/1976 | Hendren | 422/310 X |
| 4,135,868 | 1/1979 | Schainholz | 422/310 |

FOREIGN PATENT DOCUMENTS 281467 12/1927 United Kingdom ..................... 422/300

OTHER PUBLICATIONS

V. Mueller; "The Surgical Arnamentarium", Division of American Hospital Supply Corp., pp. 71, 72 (1973).

Primary Examiner—Richard L. Chiesa
Attorney, Agent, or Firm—Tilton, Fallon, Lungmus & Chestnut

[57] ABSTRACT

A surgical instrument rack useful for holding, carrying, organizing, and counting a plurality of ringhandled surgical instruments. The rack is formed of autoclavable polymeric material and includes two movable or separable members which coact with each other and with the surgical instruments to secure such instruments against release in parallel side-by-side relation with the handles and jaws (or blades) of such instruments separated slightly to facilitate sterilization of their surfaces. The structural relationship of parts responsible for the retention and automatic camming of the instruments into such slightly open positions is disclosed.

26 Claims, 4 Drawing Figures

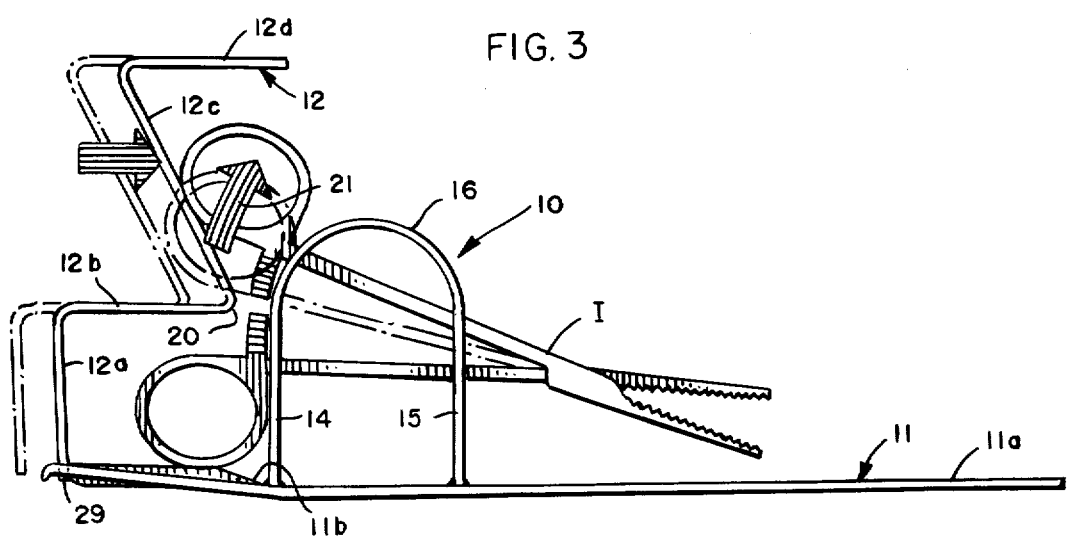
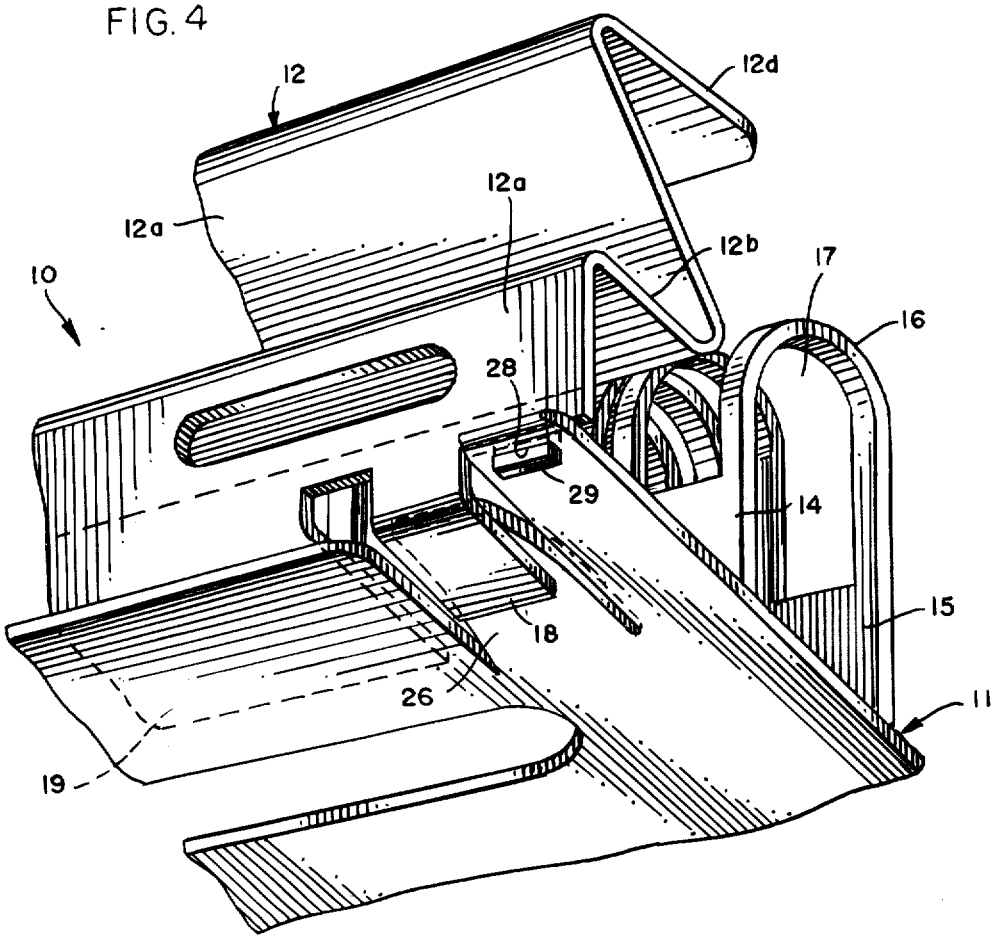

SURGICAL INSTRUMENT RACK

BACKGROUND AND SUMMARY

Surgical procedures are regularly performed using "sets" of preselected surgical instruments, each set being a collection of instruments established from experience to be useful for a given surgical procedure. For example, the surgical instruments expected to be used in an obstetrical procedure are grouped together to form a set and, as a set, are sterilized, stored on a tray or pan, and finally transported upon that tray to the operating arena when their use is required.

Ring-handled instruments (clamps, forceps, scissors, needle holders, etc.) have often been grouped together in such sets by the use of clips which are extended through the corresponding handle loops of the instruments which comprise the sets, usually with the handles of such instruments spread apart to facilitate cleaning and sterilization. Instead of clips, some hospitals use instrument racks having upstanding pegs for holding a stack of ring-handled instruments with the pegs of the rack projecting upwardly through the handle loops. In still other instances, sets of ring-handled surgical instruments have been grouped together by fashioning a makeshift clip from a pair of instruments in such a way that each set is locked together. Clips, holders, and racks typifying the structures used in the past for supporting ring-handled surgical instruments are disclosed in catalogs for such instruments, a representative catalog being The Surgical Armamentarium, V. Mueller Division of American Hospital Supply Corporation, pp. 71-72 (1973).

More recently, a wire rack has been introduced which is intended to support a multiplicity of ringhandled instruments arranged in side-by-side relation with each instrument extending along a generally vertical plane. A separate hinged rod portion of the rack is extended through the upper handle loops of all of the instruments and is then secured to the remainder of the rack in such a way that at least some of the instruments are held with their jaws in open position for sterilization. A second rod is threaded between the handles of the instruments, and in front of separator clip portions of the metal rack, to help hold the instruments in place upon the rack. Such a rack, like other known rack designs, requires the threading of a support element, in this case an elongated rod, through the handle loops in order to support the instruments as a group or set. In general, such racks have not met with widespread acceptance because they are composed of multiple parts which may be difficult to fit properly together (and relatively easy to fit improperly together), do not accommodate a wide variety of different styles and sizes of ring-handled instruments, and tend to support some instruments in a way that might cause them to be scratched or exposed to damage by reason of contact with other instruments in the same set.

A main object of this invention therefore lies in providing a rack for ring-handled surgical instruments which is relatively easy to use, and difficult to misuse or assemble improperly, and which greatly facilitates the storage, sterilization, sorting, carrying, and counting of such instruments. Additional objects involve providing a rack which protects and reduces the possibilities of damage to instruments during processing, assists the surgical team and other workers in sorting and accounting for all of the ring-handled instruments of a set, and facilitates sterilization of such instruments by automatically partially opening the jaws or blades of such instruments as the sections of the rack are latched into their closed positions. A still further object of this invention lies in providing a rack which aids in the carrying of the multiple instruments of a set without risk that one or more instruments might become inadvertently released from the rack, or swing into fully open or fully closed positions, should the rack be tipped or even inverted as it is carried.

Briefly, the rack comprises two sections or members which may be separated to load and unload the rack, and latched together to secure a multiplicity of ring-handled surgical instruments in parallel side-by-side relation with the handles and working surfaces of each instrument held slightly apart to facilitate sterilization. One of the members, a support member, has a substantially flat surface and is provided with an upstanding wall which divides that member into front and rear portions. A plurality of spaced partitions project upwardly from the wall, defining a multiplicity of spaces or compartments for receiving ring-handled instruments oriented so that each instrument extends along a substantially vertical plane with its handles projecting generally horizontally and its handle rings or loops disposed one above the other. The lower handle loop of each instrument is disposed immediately above the rear portion of the support member and directly behind the upstanding wall; hence, downward and/or forward movement of each instrument is prevented by the support member. The second member, a retaining member, interlocks with the support member to confine the instruments against rearward and/or upward movement and, in addition, cams the upper handle loop of each instrument into a raised position to open partially the jaws of that instrument. Specifically, the retaining member latches or engages the rear portion of the support member and has an overhanging cover section which is spaced above the rear portion to limit upward movement of the lower handle rings of the surgical instruments. In addition, the retaining member has a sloping camming section which is engagable with the upper rings of such instruments to cam the handles into partially opened positions, and an upper or second cover section which projects forwardly from the upper limits of the camming section and which extends over the upper handle rings of the instruments to limit opening movement of the handles thereof. The lower or first cover section and the sloping cam section merge to define a rounded leading edge which is dimensioned and positioned to be received between the upper and lower handle loops of each instrument so as to urge the upper handle loop upwardly as the retaining member is shifted into its closed or latched position.

The front portion of the support member ideally extends beneath, and forwardly beyond, the tips of the surgical instruments supported by the rack, and the upper surface of that portion is adapted to carry suitable indicia for each of the instruments of the set. The rack is constructed for individually supporting each of the instruments of that set between a pair of upstanding partitions; however, where the set includes numbers of identical instruments, the user(s) may prefer to have all instruments of the same style supported within a single compartment, thereby facilitating sorting and counting of such instruments. In that event, one or more partitions may be readily detached from the upstanding wall to provide larger compartments for receiving groups of similar instruments.

In the disclosed embodiment, the base support member is provided with a second upstanding wall parallel with and spaced in front of the first wall. The partitions are arcuate in configuration and bridge the two walls.

While different ways may be found to interconnect the two members of the rack, particularly effective results have been achieved by making such components completely separable and providing them with interfitting tabs or tongues which are dimensioned and arranged to slide together as the retaining member is urged into its latching position. In the disclosed embodiment, the retaining member is equipped with lugs or projections which are received within recesses in certain of the tongues provided by the support member when the parts are latched or locked together. Release is achieved simply by flexing the tongues away from the lugs and sliding the two members apart.

The entire rack is ideally formed from a rigid (but still slightly flexible) autoclavable polymeric material. Such a material is preferable to metal because of its relatively light weight, the adaptability of its surfaces for receiving indicia, and, in particular, the greater protection it affords against possible scratching or damage to the instruments intended to be supported by the rack.

Other features, advantages, and objects of the invention will become apparent from the specification and drawings.

DRAWINGS

FIG. 3 is a side elevational view illustrating the cooperative relationship of the members with respect to an instrument supported by the rack.

FIG. 4 is a fragmentary perspective view illustrating the interlocking tab construction of the rack.

DETAILED DESCRIPTION

Figure 1:
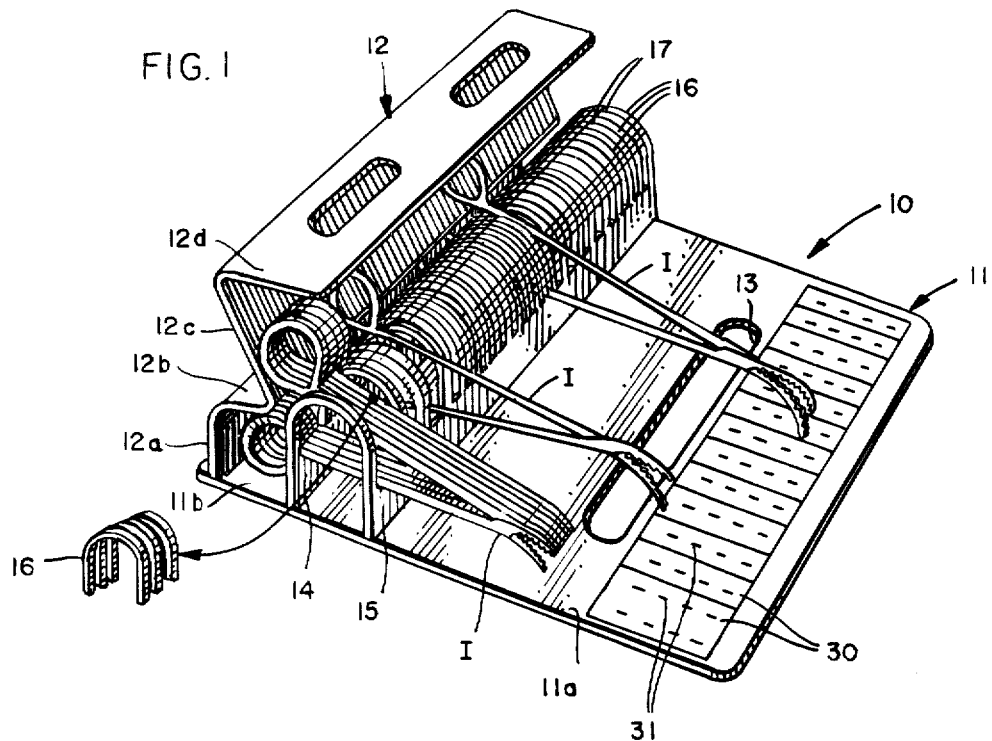
FIG. 1 is a perspective view of an assembled surgical instrument rack embodying the invention, the rack being shown supporting a limited number of instruments for purposes of illustration, and certain of the partitions being shown detached from the rack to reveal the type of user modification anticipated as part of the invention.

Referring to the drawings, the numeral 10 generally designates an instrument rack comprising a base or support member 11 and a retaining member 12. Although various fabricating materials might be used, the material of choice for both members would be a tough, relatively rigid polymeric material capable of withstanding autoclaving temperatures. For example, polypropylene or polysulfone might be advantageously used. Such plastics and others like them are more suitable than metals for the fabrication of the rack because they are less likely to scratch or otherwise damage the instruments supported by the rack and because they are non-corroding, may be intentionally cut to customize each rack to suit the needs and preferences of users (as described below), and are commonly of lighter weight and lower cost.

The support member or base 11 has generally planar front and rear portions 11a and 11b of generally rectangular configuration. Portion 11a has a smooth flat top surface which may be interrupted by one or more apertures 13 to promote the circulation of steam or other sterilizing gases and to allow fluid flow in automatic washer-sterilizers. A pair of parallel upstanding walls 14 and 15, bridged by arcuate partitioning elements or dividers 16, extend across the base and generally divide that base into its front and rear portions 11a and 11b. The arched partitions or dividers 16 are spaced apart to define compartments or slots 17 for receiving surgical instruments in the manner depicted in FIG. 1. Specifically, each compartment or slot extends vertically and has a front-to-rear directional orientation with respect to support member 11. When ring-handled surgical instruments I are properly supported by the base member 11, each such instrument extends along a generally vertical plane with its handles passing through a compartment or slot 17 and with its handle loops disposed behind wall 14 and above portion 11b. Since the partitions and the compartments defined by them are all arranged in parallel, it is believed apparent that instruments I will also tend to be parallel with each other. The spacing between walls 14 and 15, and the narrowness of the slots or compartments receiving the instruments, serve to prevent such instruments from becoming misaligned with the tip of one instrument crossing the tip of an adjacent instrument.

The height of walls 14 and 15 may be such that at least some of the instruments of a set are supported with their tips and their lower handle loops spaced slightly above the surfaces of base portions 11a and 11b (FIG. 3). In other words, at least some of the smaller instruments may be supported with their lower handles resting upon those upper edges of walls 14 and 15 which define the lower limits of the slots. In any event, each instrument is supported so that wall 14 limits forward movement of that instrument.

The instrument retaining member 12 includes a rear section 12a, a first or lower horizontal cover section 12b, an inclined camming section 12c, and an upper or second cover section 12d. In addition, the retaining member 12 has tangs or tabs 18 and 19 which project forwardly from wall section 12a. All of the wall sections and the tabs are formed integrally from the same material, preferably a relatively rigid autoclavable polymeric material as described above.

When the parts are connected as depicted in FIGS. 1 and 3, the lower cover section 12b extends horizontally and is spaced above the rear portion 11b of the base member a distance slightly greater than the width of the finger loops of the instruments I intended to be supported by the rack. While ring-handled instruments have considerable dimensional variation in other respects, their finger loop size is relatively constant. FIG. 1 illustrates a relatively small instrument having finger loops or rings of minimal size; even if such instrument had loops of maximum size, there would still be sufficient space beneath cover section 12b to accommodate the lower loop or ring of that instrument. Therefore, for all of the instruments supported by the rack, lower cover section 12b performs the function of limiting upward movement of the lower finger rings or loops of those instruments when the rack is fully assembled.

The lower cover section 12b merges smoothly with the upwardly and rearwardly inclined cam section 12c to define a tapered and rounded leading edge portion 20. When the rack is assembled, the horizontally-extending leading edge 20 projects into the space between the handle rings of each instrument with the upper ring of the instrument resting upon the inclined front surface of camming section 12c to hold the rings and jaws (or blades) of the instrument in open condition (FIG. 3). The slope of the cam section 12c is such that when the retaining member 12 is slid forwardly from the broken line position of FIG. 3 into the solid line position of that figure, the rounded leading edge 20 will first engage that ring and, with further advancement of member 12, the sloping surface of section 12c will urge or cam the upper handle loop upwardly in the direction represented by arrow 21. While a slope of approximately 60 degrees measured from the horizontal is shown in the drawings, it is believed that the slope might be varied within the range of about 30 to 75 degrees and that, if desired, the camming surface of section 12c might be non-planar or arcuate.

Upper cover section 12d constitutes a forward extension from the upper limits of cam section 12c and serves the function of limiting the extent of upward pivotal movement of the upper finger ring of each instrument. Thus, when the rack is locked in assembled condition as shown in FIGS. 1 and 3, instruments I will be retained in position, and will not even open further to any appreciable extent, even if the loaded rack were completely inverted. Since upward movement of the lower handle loops is prevented by lower cover section 12b, and since rearward movement of the instruments is limited by rear section 12a as well as by cam section 12c, inadvertent release of any ring-handled instrument from the rack is effectively prevented.

It is to be noted that such instruments are held in place without the need for threading or inserting any support members through the handle loops, a requirement characteristic of most if not all prior art systems. As a result, the mounting of instruments upon rack 10, and the removal of instruments from that rack, may be accomplished more easily and expeditiously, and with less possibility of manipulative error.

Figure 2:
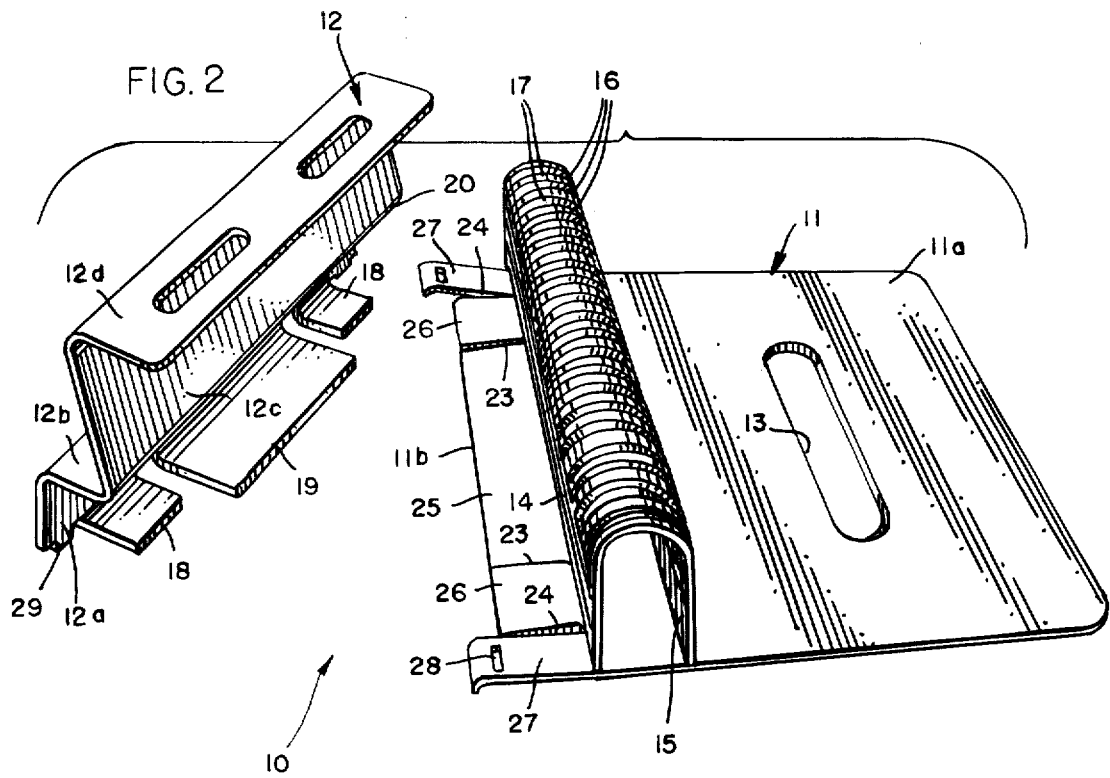
FIG. 2 is a perspective view showing the rack with the sections or members thereof in separated condition.

The two members 11 and 12 of the rack must be capable of movement into latching position so that during such movement the automatic camming action occurs as described above. While conceivably the parts might be hingedly connected so that the retaining member 12 swings through an instrument-camming arc and into latched position, a particularly effective arrangement involving a sliding action of the parts is depicted in the drawings. Referring to FIGS. 2 and 4, it will be seen that the rear portion 11b of the support section 11 is slotted at 23 and 24 to define a central tab 25, a pair of lateral tabs 26, and two outboard latching tongues or tabs 27. Each of the latching tabs 27 is provided with a recess 28 for receiving a depending lug 29 projecting downwardly from the rear wall section 12a of the retaining member 12.

When the two parts of the rack are urged together, the central tang 19 of member 12 slides over the central tab 25 of member 11, lateral tangs 18 pass beneath lateral tabs 26, and latching tabs 27 flex downwardly, by reason of camming engagement between lugs 29 and the downwardly curved surfaces at the free ends of the latching tabs, until the lugs are received within notches or recesses 28. The flexible latching tabs snap upwardly to hold the lugs within the recesses and thereby retain the parts in latched condition until separation is desired. To accomplish such separation, the user simply presses the rearwardly-projecting arcuate rear ends of the latching tabs 27 downwardly to release lugs 29, and then slides the retaining member 12 rearwardly away from support member 11.

To facilitate assembly of the parts, the various tabs may be sloped slightly, or displaced slightly above or below the plane of the other portions of the particular member from which they project, so that when the two members 11, 12 are supported upon a flat surface and are then slid upon that surface into latching relation, tang 19 will automatically move into position above tab 25, tangs 18 will pass beneath tabs 26, and lugs 29 will ride upon the upper surfaces of latching tabs 27. Thus, tang 19 may be spaced above the level of tangs 18 a distance equal to the thickness of tab 25. Similarly, the difference in levels between tabs 25 and 26 (tabs 26 being higher) may approximate the thickness of tang 19.

In the embodiment depicted in FIG. 1 the outline of the rack as defined by the outer edge of support member 11 substantially exceeds the dimensions of the instruments to be supported by the rack. The upper surface of front portion 11a below, or preferably just in front of, the tips of instruments I is adapted to receive suitable indicia representing the number and type of instrument intended to be supported in alignment with that indicia. For that purpose, the upper surface of the front portion 11a may be frosted to receive indelible ink markings, or plastic labels, either preprinted or suitably marked by the user, may be adhesively secured to that surface. In certain cases, the rack manufacturer may even preprint the top surface of the rack, either on a custom order basis or in certain cases where the particular instruments which would make up a complete set for a given operative procedure have been universally established. In the illustration given, labels 30, having suitable indicia 31 imprinted or written thereon, are adhesively secured to the rack's upper surface.

The purpose of such indicia is to assist in the sorting of ring-handled instruments before and after an operative procedure and, in particular, to help in the counting of such instruments at the end of a surgical procedure. As is well known, all such instruments must be accounted for to insure against the remote possibility that an instrument might be left within a patient. By providing a means for supporting such instruments in orderly condition, with labels indicating the number and type of instruments to be supported within any given compartment or slot, an instrument count may be quickly and easily made at the completion of a surgical procedure. It is to be understood that the rack is intended to support only those instruments intended for use in a designated surgical procedure, such instruments together forming a complete set for use in that procedure. Where a set includes a number of identical instruments, for example six Babcock Intestinal Forceps of 6¼ inches in length, or six Ochsner Artery Forceps of 8 inches in length, the personnel using the rack may elect to detach a sufficient number of partitions 16, as shown in FIG. 1, to accommodate all of the instruments of the same type and size. The legend 31 associated with the enlarged compartment might then read "6 Babcock Intestinal Forceps 6¼" or "6 Ochsner Artery Forceps 8" to reveal the total number of instruments of the same type to be received in the enlarged compartments.

The compartments or slots may be enlarged simply by cutting the polymeric material to detach the arcuate dividers or partitions at the level of the upper edges of walls 14 and 15 or, stated differently, at the level of the lower limits of partitions 16 and slots 17.

While in the foregoing we have disclosed an embodiment of the invention in considerable detail for purposes of illustration, it will be understood by those skilled in the art that many of these details may be varied without departing from the spirit and scope of the invention.

We claim:

1. A rack for supporting a multiplicity of ring-handled surgical instruments, comprising a support member having a substantially flat surface and being provided with an upstanding wall dividing said member into front and rear portions; a plurality of spaced partitions projecting upwardly from said wall, whereby, a plurality of ring-handled instruments may be supported with each instrument oriented in a generally vertical plane with its handles extending between a pair of partitions and with a lower handle ring thereof disposed directly above said rear portion and behind said wall; and a retaining member engaging said rear portion of said support member; said retaining member having a cover section spaced above said rear portion to limit upward movement of the lower handle rings of instruments carried by said support member and also having a sloping cam section engagable with the upper rings of such instruments to cam the handles thereof into partially opened condition and to limit movement of said instruments rearwardly away from said upstanding wall.

2. The rack of claim 1 in which said retaining member is detachably connected to said support member.

3. The rack of claim 2 in which said retaining member is slidably connected to said rear portion of said support member for movement generally along the plane of said surface towards and away from said upstanding wall and into and out of camming engagement with the upper handle rings of instruments carried by said support member.

4. The rack of claim 3 in which latching means is provided by said members for releasably latching said members together.

5. The rack of claim 4 in which said latching means comprises interfitting tabs provided by said members, certain of said tabs of one member being provided with lugs and certain of said tabs of the other member having recesses for releasably receiving said lugs.

6. The rack of claim 1 in which said cover section extends generally horizontally and merges at its front with said sloping cam section to define a leading edge portion adapted to be received between the upper and lower handle rings of instruments supported by said support member.

7. The rack of claim 6 in which said leading edge portion presents a rounded leading surface.

8. The rack of claim 6 in which said camming section slopes upwardly and rearwardly from said leading edge.

9. The rack of claim 6 in which said leading edge is disposed above and behind the upper limits of said upstanding wall.

10. The rack of claim 6 in which a second cover section is provided by said retaining member, said second cover section projecting forwardly from the upper limits of said camming section and being adapted to extend over the upper handle rings of instruments carried by said support member to limit opening movement of the handles of such instruments.

11. The rack of claim 1 in which said partitions are formed integrally with said upstanding wall.

12. The rack of claim 11 in which said partitions are formed of substantially rigid autoclavable polymeric material, each of said partitions being capable of detachment from said wall for selectively increasing the spacing between remaining pairs of partitions, whereby, a plurality of instruments of the same type and size may be disposed in parallel side-by-side relation within a space of increased size formed by selective detachment of one or more partitions.

13. The rack of claim 1 in which said support member is provided with a second upstanding wall parallel to and spaced in front of the first-mentioned upstanding wall, said second wall having an upper edge engagable with the handles of at least some instruments supportable by said support member to hold the jaws of said instruments slightly above said flat surface.

14. The rack of claim 13 in which said partitions are arcuate and bridge the upper edges of said first and second walls.

15. The rack of claim 14 in which said partitions are formed integrally with said first and second walls.

16. The rack of claim 15 in which said support member is formed entirely of substantially rigid autoclavable polymeric material.

17. The rack of claim 1 in which said members are formed of autoclavable and substantially rigid polymeric material.

18. The rack of claim 1 in which indicia means are applied to said support member in alignment with the spaces between said partitions to identify the surgical instruments receivable in such spaces.

19. A rack supporting a multiplicity of ring-handled surgical instruments, comprising a support member having a substantially flat surface and being provided with a pair of spaced upstanding transverse walls dividing said member into front and rear portions; said walls being bridged by a transverse series of spaced parallel arcuate dividers formed integrally with said walls and defining therebetween a plurality of instrument-receiving compartments, whereby, a plurality of ring-handled instruments may be supported with each instrument oriented in a generally vertical plane with its handles extending between a pair of dividers and with a lower handle ring thereof disposed directly above said rear portion of said support member; and a retaining member releasably connected to said rear portion; said retaining member having a lower cover section spaced above said rear portion to limit upward movement of the lower handle rings of instruments carried by said support member and also having an upwardly and rearwardly sloping cam section engagable with the upper rings of such instruments to cam the handles thereof into partially opened condition and to limit rearward movement of instruments supported by said support member.

20. The rack of claim 19 in which said retaining member is slidably connected to said rear portion of said support member for movement into and out of camming engagement with the upper handle rings of instruments carried by said support member.

21. The rack of claim 20 in which latching means is provided by said members for releasably latching said members together with said retaining member in instrument-camming position.

22. The rack of claim 19 in which said lower cover section extends generally horizontally and merges with said sloping cam section to define a rounded leading edge receivable between the upper and lower handle rings of instruments supported by said support member.

23. The rack of claim 22 in which an upper cover section is provided by said retaining member, said upper cover section projecting forwardly from the upper limits of said camming section and being adapted to extend over the upper handle rings of instruments carried by said support member to limit opening movement of the handles of such instruments.

24. The rack of claim 19 in which said support member is formed of substantially rigid autoclavable polymeric material, each of said dividers being capable of detachment from said walls for selectively increasing the width of the spacers between remaining pairs of dividers, whereby, a plurality of instruments of the same type and size may be disposed in contiguous parallel relation within a space of increased size formed by selective detachment of one or more dividers.

25. The rack of claims 19 or 24 in which both of said members are formed of substantially rigid autoclavable polymeric material.

26. The rack of claim 19 in which indicia means are applied to said support member in alignment with said spaces defined by said dividers to identify the type, size, and quantity of surgical instruments intended to be supported within said spaces.

* * * * *